(12) United States Patent
Sakaguchi

(10) Patent No.: US 8,093,447 B2
(45) Date of Patent: Jan. 10, 2012

(54) SWEAT-ABSORBENT SHEET AND DISPOSABLE DIAPER HAVING THE SAME

(75) Inventor: Satoru Sakaguchi, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 553 days.

(21) Appl. No.: 11/746,159

(22) Filed: May 9, 2007

(65) Prior Publication Data

US 2007/0265590 A1    Nov. 15, 2007

(30) Foreign Application Priority Data

May 12, 2006   (JP) ................. 2006-134522
Apr. 16, 2007   (JP) ................. 2007-107531

(51) Int. Cl.
*A61F 13/15* (2006.01)
*A61F 13/20* (2006.01)

(52) U.S. Cl. ........................ 604/359; 604/360

(58) Field of Classification Search ............ 604/359, 604/360
See application file for complete search history.

(56) References Cited

U.S. PATENT DOCUMENTS

| | | | |
|---|---|---|---|
| 4,615,937 A | | 10/1986 | Bouchette |
| 5,109,805 A | * | 5/1992 | Baldry et al. ............ 119/173 |
| 2005/0098256 A1 | * | 5/2005 | Polanco et al. ........... 156/167 |
| 2006/0025731 A1 | * | 2/2006 | Cohen .................... 604/359 |

FOREIGN PATENT DOCUMENTS

| | | |
|---|---|---|
| EP | 0389023 | 9/1990 |
| EP | 389023 A2 * | 9/1990 |
| EP | 1157679 A1 | 11/2001 |
| EP | 1967626 A1 | 9/2008 |
| GB | 958259 | 5/1964 |
| JP | 11-200245 | 7/1999 |
| JP | 2000-189454 | 7/2000 |
| JP | 2001-299811 | 10/2001 |
| JP | 2002-153507 | 5/2002 |
| JP | 2004-358099 | 12/2004 |
| WO | WO 98/19535 | 5/1998 |
| WO | WO 00/24955 | 5/2000 |
| WO | WO 2004/041312 A2 | 5/2004 |

OTHER PUBLICATIONS

Supplementary European Search Report from corresponding EP application No. 07 743 068.4 issued May 27, 2011, 4 pages.

* cited by examiner

*Primary Examiner* — Melanie Hand
(74) *Attorney, Agent, or Firm* — Brinks Hofer Gilson & Lione

(57) ABSTRACT

The present invention aims to provide a sweat-absorbent sheet containing antimicrobial medical agent ingredient and effectively absorbing sweat and a disposable diaper having the sweat-absorbent sheet.

A sweat-absorbent sheet comprises a base sheet and an antimicrobial medical agent ingredient integrated with the base sheet. The base sheet includes cellulose fiber. The medical agent ingredient is a quaternary ammonium salt. The base sheet is wetted with a solution of the quaternary ammonium salt and dried thereafter so as to be integrated with the quaternary ammonium salt. The sweat-absorbent sheet is available to a disposable diaper.

7 Claims, 2 Drawing Sheets

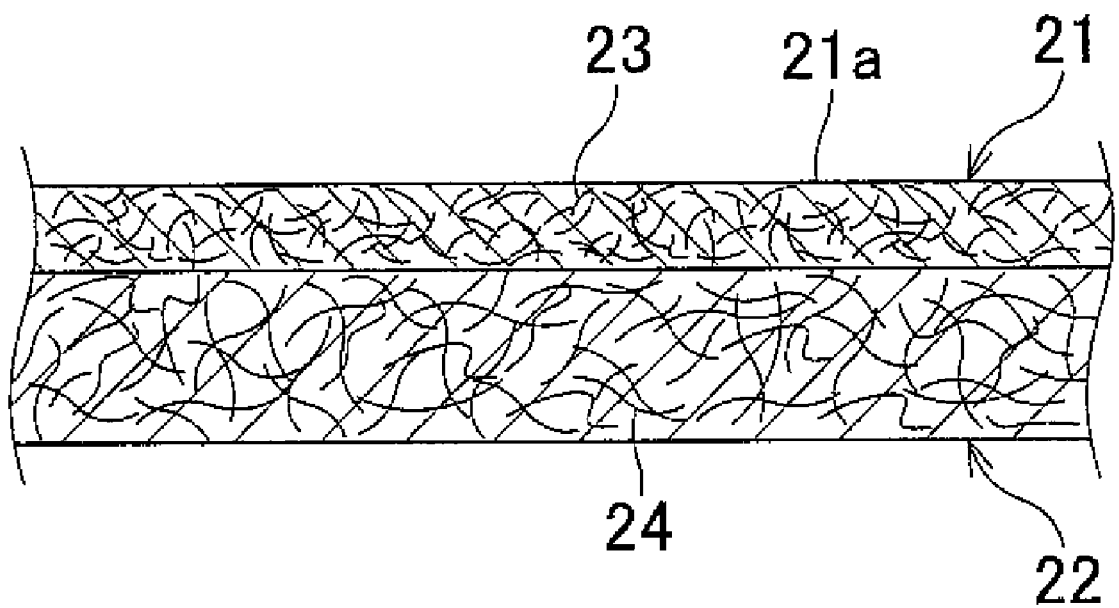

SWEAT-ABSORBENT SHEET AND DISPOSABLE DIAPER HAVING THE SAME

BACKGROUND OF THE INVENTION

The present invention relates to a sweat-absorbent sheet containing antimicrobial medical agent ingredient and a disposable diaper having the sweat-absorbent sheet.

A sweat-absorbent sheet is well known, which is adapted to be used in conjunction with a disposable wearing article such as a disposable diaper, a disposable training pants or a disposable gown. For example, a disposable diaper disclosed in Japanese Unexamined Patent Application Publication No. 2000-189454A uses a breathable sweat-absorbent sheet provided on an inner surface of end flaps. An absorbent article disclosed in Japanese Unexamined Patent Application Publication No. 2004-358099A uses a hydrophilic and breathable sweat-absorbent sheet provided on a surface of end flaps intended to contact a wearer's skin. These sweat-absorbent sheets are used to protect a wearer from various skin troubles such as heat rash and contact dermatitis which might otherwise developing during use of a disposable wearing article such as a disposable diaper. In an absorbent articles disclosed in Japanese Unexamined Patent Application Publication No. 2001-299811A and Japanese Unexamined Patent Application Publication No. 2002-153507A, regions intended to contact a wearer's skin are coated with medical agent such as aloe extract in order to protect a wearer from skin trouble such as contact dermatitis.

The sweat-absorbent sheets disclosed in Japanese Unexamined Patent Application Publication Nos. 2000-189454A and 2004-358099A, respectively, intend to bring a protecting effect to the wearer from development of heat rash by absorbing sweat. However, the protecting effect is reduced as a quantity of sweat absorbed increases. The absorbent articles disclosed in Japanese Unexamined Patent Application Publication Nos. 2001-299811A and 2002-153507A, respectively, use medical agents coated on an air-through non-woven fabric of composite fiber or on a non-woven fabric of long fiber. While such measures can protect the wearer from the skin trouble such as heat rash or contact dermatitis, it will be difficult to deal with heavy sweat so as to make the wearer feel a dryness because the non-woven fabrics used therein are not sweat-absorbent.

SUMMARY OF THE INVENTION

In view of problems as described in the above, it is a first principal object of the present invention to provide a sweat-absorbent sheet adapted to, during use of this sweat-absorbent sheet in contact with the wearer's skin, make the wearer's sweaty skin experience a feeling of dryness and to constrain proliferation of bacteria and/or fungi considered to cause heat rash to develop. In addition, it is a second principal object of the present invention to provide a disposable diaper having the sweat-absorbent sheet.

The first object set forth above is achieved, according to the present invention, by a sweat-absorbent sheet including a base sheet formed by a fibrous assembly containing water-absorbent fiber and medical agent ingredient integrated with the base sheet. The sweat-absorbent sheet is characterized in that the water-absorbent fiber includes a cellulosic fiber and the medical agent ingredient is a quaternary ammonium salt. The base sheet is integrated with said quaternary ammonium salt after a wetting process with a solution of the quaternary ammonium salt and a drying process following said wetting process.

According to one preferred embodiment of the invention, the quaternary ammonium salt is any one of cetylpyridinium chloride, benzalkonium chloride and benzethonium chloride. According to another preferred embodiment of the invention, wherein a quantity of the quaternary ammonium salt integrated with the base sheet is in a range of 0.012 to 0.176 wt % with respect to a weight of the base sheet. According to further another embodiment of the invention, a quantity of the quaternary ammonium salt integrated with said base sheet is in a range of 0.029 to 0.088 wt % with respect to the weight of the base sheet. According to further another embodiment of the invention, the base sheet is a tissue paper made from pulp fiber as the cellulosic fiber.

The second object set forth above is achieved, according to the present invention, by a disposable diaper having a front waist region, a rear waist region, a crotch region interposed between said front and rear waist region, wherein the disposable diaper comprises an inner surface to contact a skin of a wearer of the disposable diaper, an outer surface to contact clothes of the wearer, and a sweat-absorbent sheet attached to the inner surface of at least the rear waist region of the front waist region, the rear waist region and the crotch region, and the sweat-absorbent sheet comprises a base sheet formed by a fibrous assembly including a water-absorbent fiber and a quaternary ammonium salt integrated with the base sheet.

The sweat-absorbent sheet according to the present invention comprises the cellulose fiber of the base sheet and the quaternary ammonium integrated with the base sheet so that the cellulose fiber which is hydrophilic sufficiently absorbs sweat to make the wearer feel a dryness. In addition, the quaternary ammonium salt is smoothly eluted into sweat from the cellulose fiber wetted with the sweat and serving as a carrier for the quaternary ammonium salt so as to constrain proliferation of epidermatic staphylococcus on the sweaty skin and thereby to protect the wearer from development of heat rush.

In the embodiment of the invention wherein the quaternary ammonium salt is any one of cetylpyridirium chloride, benzalkonium chloride and benzethonium chloride, the medical agent ingredient is easy to get.

In the embodiment of the invention wherein a quantity of the quaternary ammonium salt is in a range of 0.012 to 0.176 wt % with respect to a weight of the base sheet, the sweat-absorbent sheet of the present invention will constrain proliferation of bacteria and/or fungi and will irritate the wearer's skin.

In the embodiment of the invention wherein the base sheet formed by the fibrous assembly is a tissue paper formed by the pulp fiber, the pulp fiber will serve as a good carrier for the quaternary ammonium salt.

The disposable diaper according to the present invention which has the sweat-absorbent sheet in the inner surface of the rear waist region will protect an infant wearing the diaper from a development of heat rush on his or her lumbar region.

BRIEF DESCRIPTION OF THE DRAWINGS

FIG. 2 is a partial sectional view of a sweat-absorbent sheet.

DETAILED DESCRIPTION OF THE PREFERRED EMBODIMENTS

Figure 1:
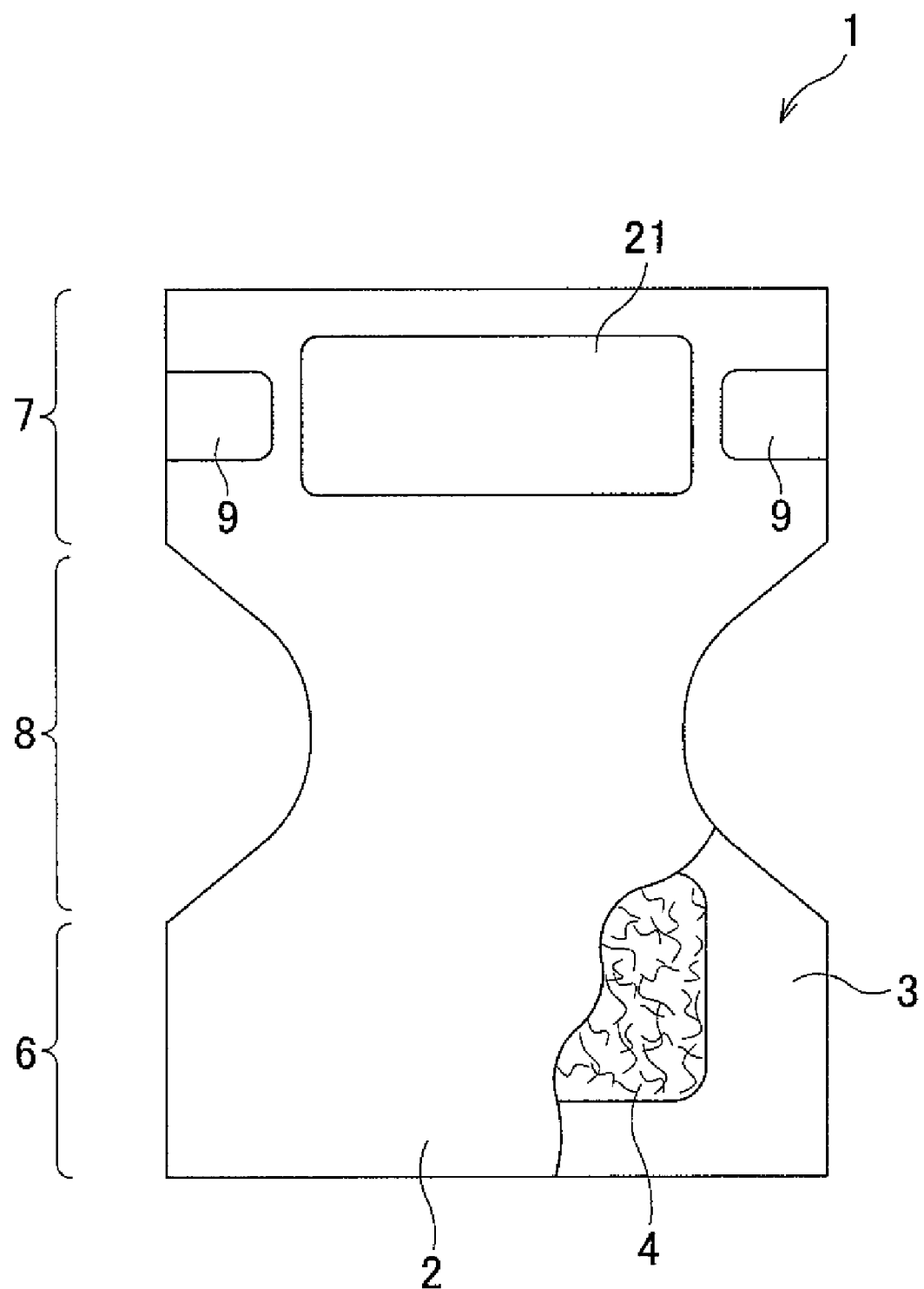
FIG. 1 is a partially cutaway plan view showing a disposable diaper as developed in a flattened condition.

Details of the sweat-absorbent sheet according to the present invention will be more fully understood from the description given hereunder in reference with the accompanying drawings.

FIG. 1 is a partially cutaway plan view showing a disposable diaper 1. The diaper 1 has a liquid-pervious topsheet 2, a liquid-impervious backsheet 3 and a liquid-absorbent core 4 sandwiched between these two sheets 2, 3 so as to define a front waist region 6, a rear waist region 7 and a crotch region 8 cooperating together to cover a diaper wearer's body. The rear waist region 7 is provided on transversely opposite edges thereof with fasteners 9 used to connect the front and rear waist regions 6, 7 to each other. The topsheet 2 provides the diaper 1 with an inner surface to contact a wearer's skin (not shown) and the backsheet 3 provide the diaper 1 with an outer surface to contact wearer's clothes (not shown).

The diaper 1 constructed in this manner further includes a sweat-absorbent sheet 21 attached together with a reinforcing sheet 22 (See FIG. 2) to a part of the topsheet 2 in the rear waist region 7 using appropriate adhesive or welding technique. Sweat secreted over a lumbar region of the diaper wearer is effectively absorbed by the sweat-absorbent sheet 21 so that the wearer of this diaper 1 may enjoy a dry condition and may be protected from heat rash due to the sweat.

FIG. 2 is a partial sectional view showing the sweat-absorbent sheet 21 shown in FIG. 1 together with the reinforcing sheet 22. These sheets 21, 22 are integrally laminated in a manner that the sweat-absorbent sheet 21 comes in direct contact with the diaper wearer's skin. While the sweat-absorbent sheet 21 comprises a base sheet 21a which is a carrier and a medical agent ingredient (not shown) on the carrier, the base sheet 21a is a fibrous assembly including cellulose fiber, preferably pulp fiber by a ratio of 5 to 20 g/m$^2$. And the fibrous assembly may include thermoplastic synthetic fiber such as polyester fiber or composite fiber consisting of polypropylene as a core component and polyethylene as a sheath component by 0 to 90 wt % with respect to the cellulose fiber. In the illustrated embodiment, a tissue paper consisting of pulp fiber 23 alone which has a basis weight of 17 g/m$^2$ is used as the base sheet 21a. The sweat-absorbent sheet 21 is obtained by wetting the base sheet 21a with a water or alcoholic solution of the quaternary ammonium salt having a controlled concentration thereof and then drying the base sheet 21a wherein the base sheet is integrated with a controlled quantity of the quaternary ammonium salt. The quaternary ammonium salt is integrally deposited on or chemically bonded to the pulp fiber 23 serving as a carrier.

The quaternary ammonium salt is used as a medical agent ingredient to constrain of bacteria and/or fungi and including, for example, cetylpyridinium chloride, benzalkonium chloride, benzethonium chloride, alkylpyridinium chloride, alkyltrimetylammonium chloride, dialkyl dimethylammmonium chloride, hexadecyltrimethylammonium bromide, didecyldimethylammonium chloride, decylisononyldimethylammonium floride, hexadecylpyridinium chloride, 4,4'-(tetramethyl-enedicarboniumamino)bis(1-decylpyridinium bromide), N,N'-hexamethylenebis(4-carbamoyl-1-decylpyridinium bromide).

The base sheet 21a can be wetted with a solution of the medical agent ingredient by spraying the solution to the base sheet 24 or immersing the base sheet 24 into the solution.

The reinforcing sheet 22 is used to maintain a structure of the sweat-absorbent sheet 21 and is preferably formed by non-woven fabric of thermoplastic fiber 24 such as air-through non-woven fabric or spun-bonded non-woven fabric. More preferably, the thermoplastic fiber 24 is thermally crimped composite fiber and the reinforcing sheet 22 is flexible and well breathable. Such a reinforcing sheet 22 is attached to the sweat-absorbent sheet 21 using bonding means such as adhesive or welding technique, or fiber interlacing means such as jetting of high pressure columnar water or needle punching. The reinforcing sheet 22 is attached to the topsheet 2 using bonding means such as adhesive or welding technique.

According to one conventional popular theory, heat rash develops when sweat pores are choked up as a result of heavy sweating until sweat seeps through superficial skin to cause inflammation. However, the inventor of the present invention has found that the heat rash may be potentially caused by choking up the sweat ducts by products of epidermal staphylococcal bacteria proliferating on the sweaty skin. Additionally, the inventor has found a positive prospect that an appropriate quantity of cationic antimicrobial agent such as a quaternary ammonium salt, an example of which is cetylpyridinium chloride, or poly-cationic antimicrobial agent, an example of which is polylysine, may be used so as to exist together with the epidermal staphylococcal bacteria in order to prevent the epidermal staphylococcal bacteria from proliferating and an irritation of user's skin thereby. The sweat-absorbent sheet 21 illustrated by FIGS. 1 and 2 has been made on the basis of such a prospect. The sweat-absorbent sheet 21 is made of pulp fiber 23 which is sufficiently water-absorbent, on one hand, and tends to be firmly integrated with the cationic antimicrobial agent, on the other hand. Such a pulp fiber 23 rapidly absorbs sweat, giving the wearer's skin a feeling of dryness, and the quaternary ammonium salt integrated with the pulp fiber 23 is gradually eluted into the sweat. In this way, the sweat-absorbent sheet 21 prevents the epidermal staphylococcal bacteria from proliferating.

Table 1 shows quantities (g/l) of each medical agent ingredient eluted from various sweat-absorbent sheets for test purpose when they were left for 4 hours in distilled water (DW) or in physiologic saline (NaClaq) of 0.5 wt % substantially corresponding to a salinity of sweat. The base sheets of the sweat-absorbent sheets for test purpose were 3.4 g (grams) of a tissue paper whose base weight was 17 g/m$^2$. The base sheets were left in various aqueous solutions respectively containing the medical agent ingredient of different concentrations and then dried to get sweat-absorbent sheets for test purpose which were integrated with different quantities of each medical agent ingredient. Then, the sweat-absorbent sheets were left in 35 ml of distilled water or physiologic saline serving as an elute at 20 C° for 4 hours to elute the medical agent ingredients. The quantities (g/l) of the medical agent ingredients present in the respective elutes were measured by HPLC on CrestPac C18S column. In Table 1, the quantities of the medical agent ingredients were almost the same between the distilled water and the physiologic saline.

TABLE 1

| Medical agent ingredient | Quantity of eluted medical agent ingredient | | Quantity of medical agent ingredient | | | | | | | |
|---|---|---|---|---|---|---|---|---|---|---|
| | | | g/m² | | | | | | | |
| | | | 0.0075 | | 0.015 | | 0.03 | | 0.06 | |
| | | | wt % | | | | | | | |
| | | | 0.044 | | 0.088 | | 0.176 | | 0.353 | |
| | Immersion liquid | | DW | NaClaq | DW | NaClaq | DW | NaClaq | DW | NaClaq |
| cetylpyridinium chloride | Quantity of eluted medical agent ingredient after 4 hours (g/l) | 1 | 0.0042 | 0.0058 | 0.0057 | 0.0094 | 0.0119 | 0.0182 | — | — |
| | | 2 | 0.0050 | 0.0089 | 0.0081 | 0.0102 | 0.0186 | 0.0166 | — | — |
| | | 3 | 0.0023 | 0.0035 | 0.0045 | 0.0068 | 0.0144 | 0.0131 | — | — |
| | | 4 | 0.0034 | 0.0046 | 0.0055 | 0.0077 | 0.0166 | 0.0139 | — | — |
| | | Average | 0.0037 | 0.0057 | 0.0060 | 0.0085 | 0.0154 | 0.0154 | — | — |
| benzalkonium chloride | Quantity of eluted medical agent ingredient after 4 hours (g/l) | 1 | 0.017 | 0.011 | 0.043 | 0.026 | 0.073 | 0.045 | 0.120 | 0.160 |
| | | 2 | 0.018 | 0.010 | 0.009 | 0.024 | 0.082 | 0.045 | 0.130 | 0.180 |
| | | 3 | 0.015 | 0.010 | 0.041 | 0.021 | 0.098 | 0.043 | 0.190 | 0.110 |
| | | Average | 0.017 | 0.010 | 0.031 | 0.024 | 0.084 | 0.044 | 0.147 | 0.150 |
| benzethonium chloride | Quantity of eluted medical agent ingredient after 4 hours (g/l) | 1 | 0.017 | 0.018 | 0.048 | 0.046 | 0.120 | 0.074 | 0.210 | 0.160 |
| | | 2 | 0.017 | 0.019 | 0.045 | 0.043 | 0.110 | 0.087 | 0.210 | 0.160 |
| | | 3 | 0.020 | 0.020 | 0.043 | 0.042 | 0.084 | 0.085 | 0.210 | 0.160 |
| | | Average | 0.018 | 0.019 | 0.045 | 0.044 | 0.105 | 0.082 | 0.210 | 0.160 |

DW: distilled water
NaClaq: 0.5% saline

Table 2 shows also a result of an upper arm test conducted by maintaining the various sweat-absorbent sheets each of 5×5 cm in close contact with upper arms of 10 healthy men for 24 hours and observing skin conditions. "Quantity of eluted medical ingredient after 4 hours (g/l)" in Table 2 shows quantities of eluted medical agent ingredients from the sweat-absorbent sheets for test purpose in the same test as in Table 1. Concerning a result of observation about a preventive effect against development of the heat rash, "effective" indicates a case in which the effect has been confirmed on 8 or more persons among 10 persons, "slightly effective" indicates a case in which the effect has been confirmed on 6 or more persons among 10 persons and "ineffective" indicates a case in which no effect has been confirmed on 5 or more persons among 10 persons. Concerning a result of observation about abnormality occurring on a skin, "not abnormal" indicates a case in which no abnormality has been observed on all 10 persons, "slightly abnormal" indicates a case in which no abnormality has been observed on 8 to 9 persons among 10 persons. Based on such a result of the observation about the skin abnormality, a preferable quantity of the quaternary ammonium salt is less than 0.176 wt % with respect to a weight of the base sheet 21a and a more preferable quantity of the quaternary ammonium salt is less than 0.088 wt %. Based on the observation about the preventive effect against the development of the heat rash, a preferable quantity of the quaternary ammonium salt is more than 0.012 wt % with respect to the weight of the base sheet 21a and a more preferable quantity of the quaternary ammonium salt is more than 0.029 wt %.

TABLE 2

| | Properties of sweat-absorbent sheet | | | | | |
|---|---|---|---|---|---|---|
| | medical agent ingredient per base sheet | | Quantity of eluted medical agent ingredient (g/l) | | Upper arm skin test | |
| Medical agent ingredient | (g/m²) | (wt %) | DW | NaClaq | Preventive effect against heat rash | Skin abnormality |
| cetylpridinium chloride | 0.0010 | 0.0060% | 0.0005 | 0.0005 | ineffective | not abnormal |
| | 0.0050 | 0.029% | 0.0025 | 0.0027 | slightly effective | not abnormal |
| | 0.0075 | 0.044% | 0.0037 | 0.0057 | effective | not abnormal |
| | 0.010 | 0.059% | ND | ND | effective | not abnormal |
| | 0.015 | 0.088% | 0.006 | 0.0085 | effective | not abnormal |
| | 0.030 | 0.176% | 0.0154 | 0.0154 | effective | slightly abnormal |
| | 0.060 | 0.353% | 0.029 | 0.032 | — | abnormal |
| benzalkonium chloride | 0.0015 | 0.009% | 0.0037 | 0.0034 | ineffective | not abnormal |
| | 0.0020 | 0.012% | 0.0050 | 0.0049 | slightly effective | not abnormal |
| | 0.0050 | 0.029% | 0.0125 | 0.0121 | effective | not abnormal |
| | 0.0075 | 0.044% | 0.017 | 0.0100 | effective | not abnormal |
| | 0.015 | 0.088% | 0.031 | 0.024 | effective | not abnormal |
| | 0.03 | 0.176% | 0.084 | 0.044 | effective | not abnormal |
| | 0.04 | 0.235% | 0.0998 | 0.0920 | effective | slightly abnormal |
| | 0.06 | 0.353% | 0.147 | 0.150 | effective | slightly abnormal |
| benzethonium chloride | 0.0010 | 0.006% | 0.0035 | 0.0027 | ineffective | not abnormal |
| | 0.0025 | 0.015% | 0.0087 | 030090 | slightly effective | not abnormal |
| | 0.0030 | 0.018% | 0.0104 | 0.0081 | effective | not abnormal |
| | 0.0050 | 0.029% | 0.017 | 0.0170 | effective | not abnormal |

TABLE 2-continued

| | Properties of sweat-absorbent sheet | | | | | |
|---|---|---|---|---|---|---|
| | medical agent ingredient per base sheet | | Quantity of eluted medical agent ingredient (g/l) | | Upper arm skin test | |
| Medical agent ingredient | (g/m²) | (wt %) | DW | NaClaq | Preventive effect against heat rash | Skin abnormality |
| | 0.0075 | 0.044% | 0.018 | 0.0190 | effective | not abnormal |
| | 0.0150 | 0.088% | 0.045 | 0.0440 | effective | not abnormal |
| | 0.03 | 0.176% | 0.104 | 030820 | effective | slightly abnormal |
| | 0.06 | 0.353% | 0.210 | 0.160 | effective | abnormal |

DW: distilled water
NaClaq: 0.5% saline

In the case of the embodiment of the present invention wherein the sweat-absorbent sheet 21 has a high tensile strength enough to maintain its integrity even when it absorbs sweat, it is unnecessary to use the reinforcing sheet 22. Obviously, the sweat-absorbent sheet 21 is useful in conjunction not only with the disposable diaper as illustrated but also with other various wearing articles such as training pants or incontinence pants. Although the sweat-absorbent sheet 21 is preferable to be used in a combination with such wearing articles, the sweat-absorbent sheet 21 also can be used independently.

The present invention thus permits the sweat-absorbent sheet and the disposable diaper having the sweat-absorbent sheet providing the preventive effect against development of heat rash to be made.

The entire discloses of Japanese Patent Application Nos. 2006-134522 filed on May 12, 2006 and 2007-107531 filed on Apr. 16, 2007, respectively, including specification, drawings and abstract are herein incorporated by reference in their entirety.

What is claimed is:

1. A disposable diaper having a front waist region, a rear waist region, a crotch region interposed between said front and rear waist regions, said disposable diaper comprising:
   a liquid-pervious topsheet that defines an inner surface of said diaper to contact skin of a wearer of said disposable diaper and an opposite outer surface;
   a liquid-impervious backsheet that defines an outer surface of said diaper to contact clothes of said wearer and an opposite inner surface;
   a liquid-absorbent core positioned between the liquid-pervious topsheet and the liquid impervious backsheet and in contact with the outer surface of the liquid-pervious topsheet and with the inner surface of the liquid-impervious backsheet; and
   a sweat-absorbent sheet attached to a part of said inner surface of said topsheet of at least said rear waist region as selected from said front waist region, said rear waist region and said crotch region, wherein said sweat-absorbent sheet is exposed to the skin of the wearer and comprises a base sheet formed by a fibrous assembly including water-absorbent fiber, cellulosic fiber included in said water-absorbent fiber, and a quaternary ammonium salt integrated with said base sheet.

2. The sweat-absorbent sheet according to claim 1, wherein said quaternary ammonium salt is any one of cetylpyridinium chloride, benzalkonium chloride and benzethonium chloride.

3. The sweat-absorbent sheet according to claim 1, wherein a quantity of said quaternary ammonium salt integrated with said base sheet is in a range of 0.012 to 0.176 wt % with respect to a weight of said base sheet.

4. The sweat-absorbent sheet according to claim 1, wherein a quantity of said quaternary ammonium salt contained in said base sheet is in a range of 0.029 to 0.088 wt % with respect to a weight of said base sheet.

5. The sweat-absorbent sheet according to claim 1, wherein said base sheet is a tissue paper made from pulp fiber as said cellulosic fiber.

6. The disposable diaper according to claim 1, wherein said sweat-absorbent sheet is integrally laminated with a reinforcing sheet which is formed of non-woven fabric of thermoplastic fiber and attached to said inner surface of said topsheet.

7. The disposable diaper according to claim 6, wherein said sweat-absorbent sheet is integrally laminated with said reinforcing sheet which is formed of said non-woven fabric of thermoplastic fiber which is thermally crimped fiber.

* * * * *